(12) United States Patent  
Pohjoispuro et al.

(10) Patent No.: US 8,073,100 B2  
(45) Date of Patent: Dec. 6, 2011

(54) PANORAMIC X-RAY APPARATUS

(75) Inventors: Petri Pohjoispuro, Espoo (FI); Timo Müller, Helsinki (FI)

(73) Assignee: Planmeca Oy, Helsinki (FI)

( * ) Notice: Subject to any disclaimer, the term of this patent is extended or adjusted under 35 U.S.C. 154(b) by 103 days.

(21) Appl. No.: 12/450,274

(22) PCT Filed: Mar. 20, 2008

(86) PCT No.: PCT/FI2008/050131
§ 371 (c)(1),
(2), (4) Date: Oct. 13, 2009

(87) PCT Pub. No.: WO2008/113894
PCT Pub. Date: Sep. 25, 2008

(65) Prior Publication Data
US 2010/0091942 A1    Apr. 15, 2010

(30) Foreign Application Priority Data
Mar. 20, 2007   (FI) .................................. 20075182

(51) Int. Cl.
*A61B 6/14*    (2006.01)
(52) U.S. Cl. .......................................... 378/38; 378/197
(58) Field of Classification Search .............. 378/38–40, 378/193–198
See application file for complete search history.

(56) References Cited

U.S. PATENT DOCUMENTS

| 4,802,198 A | 1/1989 | Guenther et al. ............. 378/197 |
| 6,052,428 A * | 4/2000 | Nakano et al. ................. 378/38 |

FOREIGN PATENT DOCUMENTS

| JP | 09-122118 | 11/1995 |
| SE | 201 217 A | 7/1962 |
| WO | WO 90/14748 | 5/1990 |

OTHER PUBLICATIONS

International Search Report mailed Jun. 27, 2008.
Search Report from Finland mailed Jan. 9, 2008.
TEK: Keksintöjen kirja, Toivonen Ret al. (toim), (1981) pp. 44-45, with English abstract.
Facta 2001, Numminen M et al., (toim), (1989) pp. 484-485, with English abstract.
Tietosanakirja, kymmenes osa, (1919) pp. 1627-1628, with English abstract.
Bonniers Lexikon 2, (1997) pp. 247, with English abstract.
Lilla uppslagsboken 1, (1967), pp. 956-958, with English abstract.
Wikipedia: Pulley (2007), in English.

* cited by examiner

*Primary Examiner* — Courtney Thomas
(74) *Attorney, Agent, or Firm* — Stites & Harbison PLLC; Juan Carlos A. Marquez, Esq.

(57) ABSTRACT

A panoramic X-ray apparatus, comprising at least a support element (2), a patient support (9) arranged to be movable in a vertical direction and an imaging station (4a). The panoramic X-ray apparatus has a support structure (4) arranged to support at least the imaging station (4a), and it has an actuator (15) producing a vertical linear motion for moving at least the imaging station (4a) to different height positions. The panoramic X-ray apparatus comprises a transmission mechanism (28) which affects the velocity/travel distance of the vertical movement of the imaging station (4a) and which is connected at least to the actuator (15) and either to the aforesaid support structure (4) or to the aforesaid support element in such manner that the velocity/travel distance of the vertical movement of the imaging station (4a) is substantially greater than the velocity/travel distance of the motion imparted by the actuator (15) to the transmission mechanism (28).

15 Claims, 4 Drawing Sheets

PANORAMIC X-RAY APPARATUS

Figure 1:
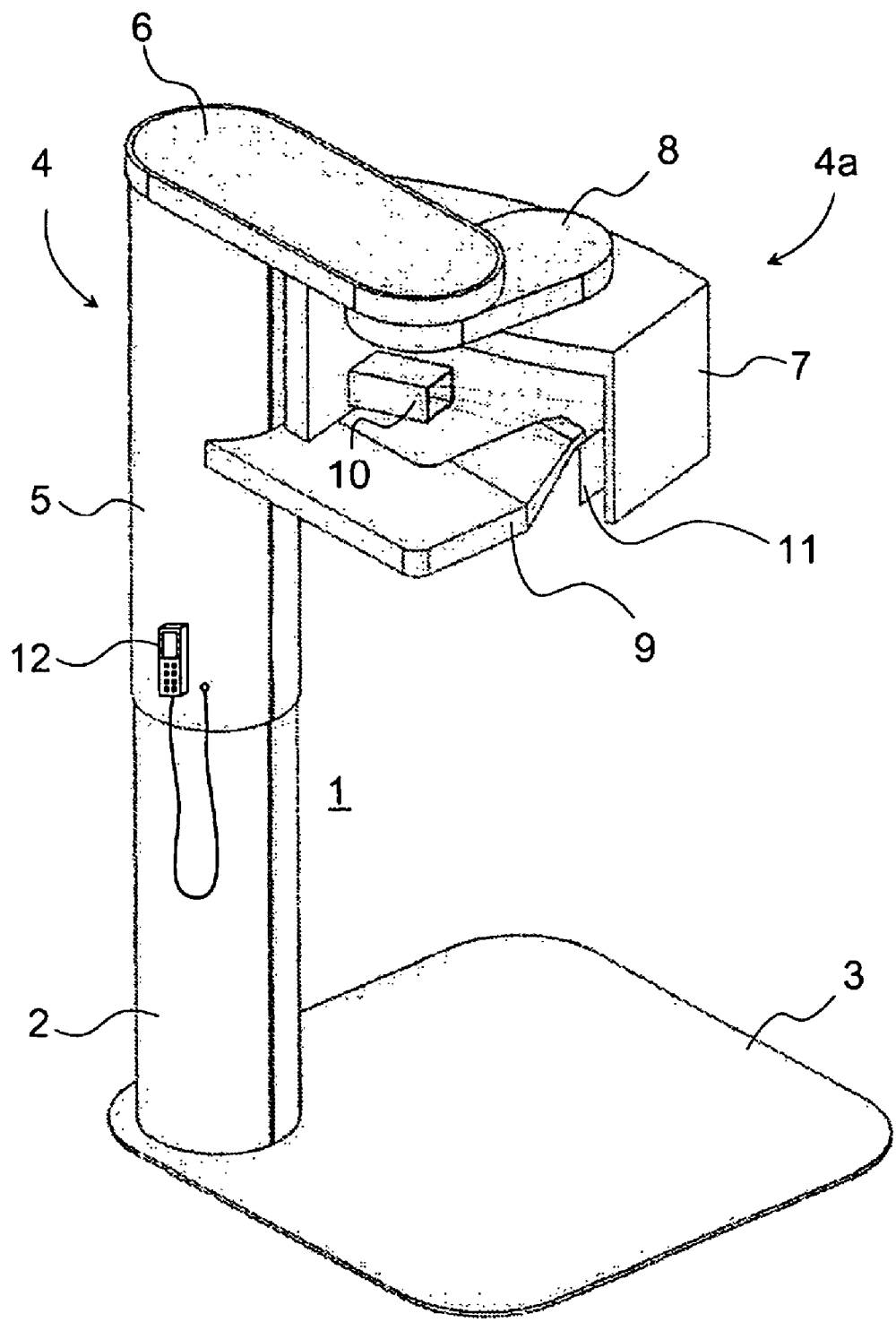

The present invention relates to a panoramic X-ray apparatus as defined in the preamble of claim 1, comprising at least means for transferring an imaging station to different height positions.

Dental panoramic X-ray imaging is generally understood as meaning a specific X-ray imaging method applicable for imaging the dental arch, wherein the dental arch is scanned with a narrow vertical X-ray beam by keeping the beam substantially perpendicularly oriented relative to the dental arch throughout the scanning action while simultaneously turning the radiation source and the receiver of image information relative to the object being imaged. Panoramic X-ray apparatuses based on this principle are used for imaging e.g. a patient's teeth, jaw bones and joints as well as oral cavity and maxillary sinuses. For the imaging, the patient support means and the imaging arms arrangement of the apparatus are driven to an appropriate height with respect to patient's height. Hereinafter, the term 'imaging station' is used to denote the overall assembly consisting of at least the imaging arm arrangement, the imaging means, such as an X-ray source and an image information receiving means, and the elements supporting and moving the imaging arm arrangement. This height adjustment is generally performed as safely, quickly and smoothly as possible. The aim is that patient positioning would not take too much time and that the positioning range would be sufficient for patients of any size.

In prior-art solutions, a panoramic X-ray apparatus is known in which the above-mentioned height adjustment is implemented on a simple counterweight principle. Then, for instance at the upper end of a support pillar of the apparatus there is an actuator fitted to rotate a small pulley with a cable or chain set to run over it, supporting a vertically movable patient support and an imaging arm assembly. The first end of the supporting cable is attached to a vertically movable part and the second end is attached to a counterweight, whose mass has been selected to be appropriate in relation to the mass of the vertically movable part. To drive such a mechanism, a low-power actuator is sufficient, because the actuator practically only has to work against inertia forces. However, a problem with this type of apparatus implemented with a counterweight is the relatively heavy counterweight itself, because it increases the total mass of the apparatus and causes expenses. A further problem is that, e.g. due to its own height, the counterweight restricts vertical adjustment of the apparatus. In this case e.g. the support pillar must therefore be made higher, which again increases the total mass and, due to the length of the support pillar, requires a larger transportation package for the apparatus, which is more expensive and more difficult to handle than the transport packages of devices implemented using different constructions.

Previously known are also solutions for adjusting the height of the patient support and imaging arm assembly wherein the vertical motion is implemented using a long vertical threaded bar rotated by an actuator and disposed inside the panoramic apparatus. In this case, for instance, the vertically movable patient support and imaging arm assembly are connected to a vertically immovable threaded bar placed inside the support pillar of the panoramic apparatus with the help of one or more non-rotatable nut-like elements, so that, when the threaded bar is rotated by the actuator about its longitudinal axis, the patient support and imaging arm assembly are moved vertically. The threaded bar may just as well be included in the movable part and the nut-like elements in the immovable part. A problem with these prior-art solutions is that, even if the support pillar could be reduced to a suitable length, it is difficult to achieve a sufficient speed of movement of the patient support and imaging arm assembly in an economic manner. To attain a sufficient speed, it would be necessary to use a powerful and substantially robust and consequently expensive actuator to rotate the threaded bar. An actuator like this, together with its expensive control system, is voluminous and both complicated and heavy in construction.

The object of the present invention is to provide a new type of solution regarding the above-described problems and to achieve an inexpensive and simple panoramic X-ray apparatus in which the means for changing the vertical position of the imaging station is relatively light while still enabling the imaging station to be moved to different height positions sufficiently fast. A further object is to create a construction wherein an essentially small movement of the actuator producing vertical motion causes at least the imaging station to move through an essentially long travel distance that is sufficient for the imaging of patients of different heights. One of the aims is thus e.g. to achieve an imaging-station travel distance that is sufficient for patients of practically any size, i.e. a vertical movement of about one meter. The panoramic X-ray apparatus of the invention is characterized by what is disclosed in the characterizing part of claim 1. Certain other embodiments of the invention are characterized by what is disclosed in the other claims.

The solution of the invention provides the advantage that the total mass of the panoramic X-ray apparatus can be kept relatively small while still achieving a sufficient speed of vertical motion and a sufficient vertical travel distance of the imaging station. A further advantage is that the aforesaid sufficient speed and travel distance of the imaging station are achieved using an actuator that needs not be fast in itself and the travel distance directly produced by it needs not be as long as the travel distance through which it causes the imaging station to move. It is sufficient for the actuator to be able to produce the required power. Basically, this type of actuators can be found on the market for a considerably more inexpensive price than actuators directly producing a fast movement. Another advantage is that, in a construction according to the invention, the upper edge of the vertically movable carriage, depending on its supporting and guiding structures, may rise a considerable distance above the upper end of the support pillar of the apparatus, allowing the support pillar to be constructed to a suitable length in view of e.g. export packages, and yet the power means producing vertical motion need not be e.g. as powerful as in the above-mentioned prior-art threaded-bar solutions.

Figure 2:
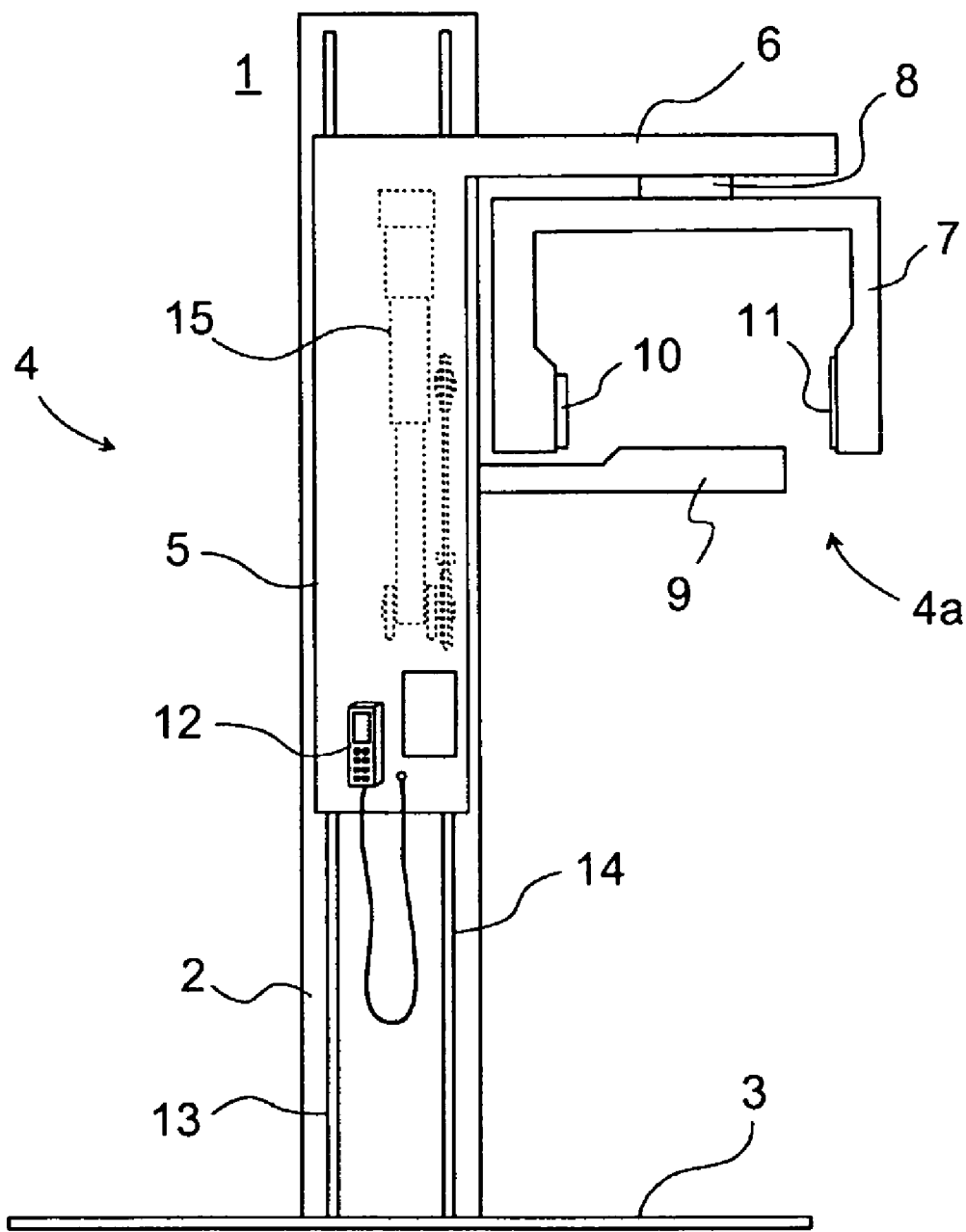
Figure 3:
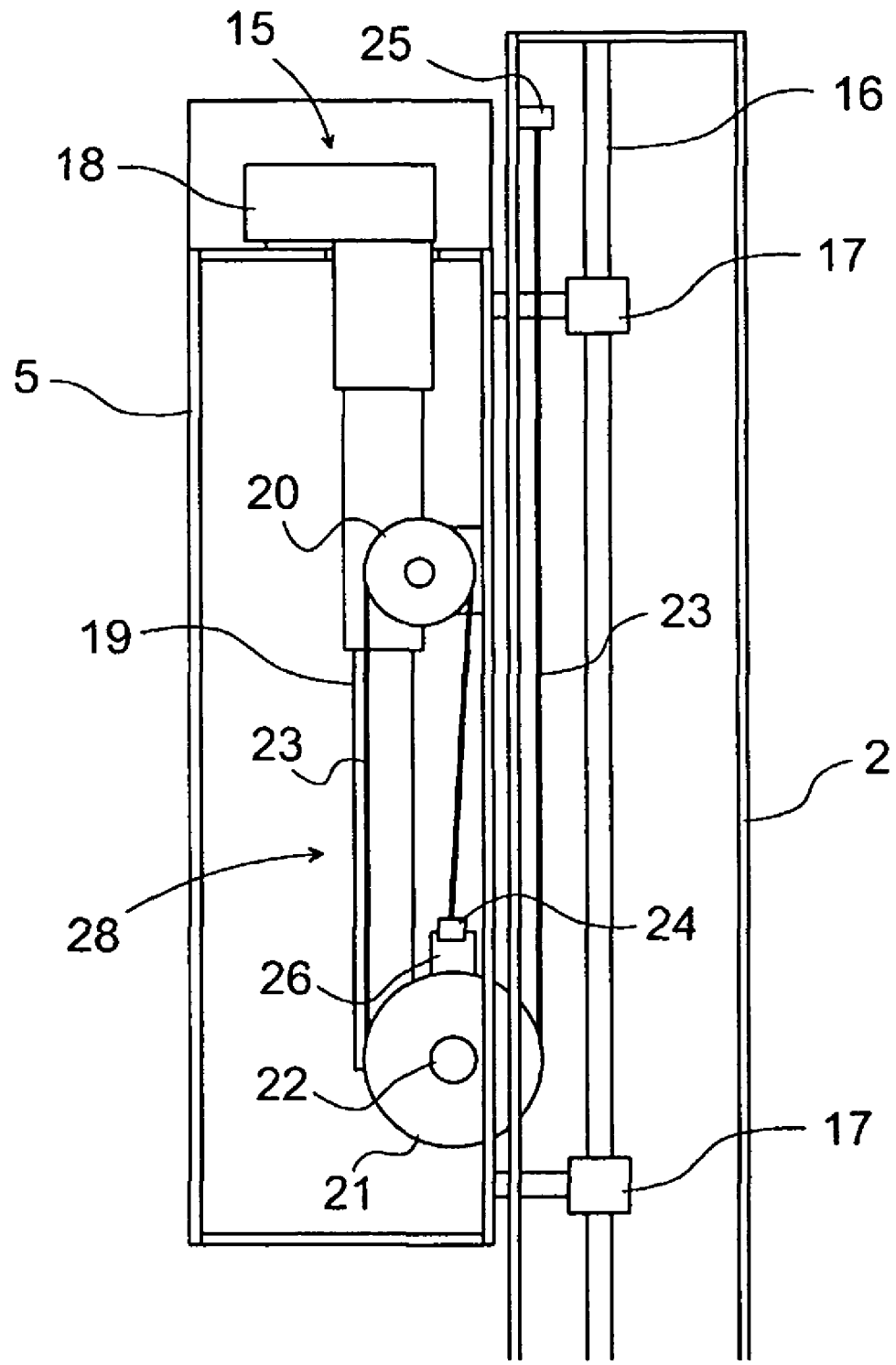
Figure 4:
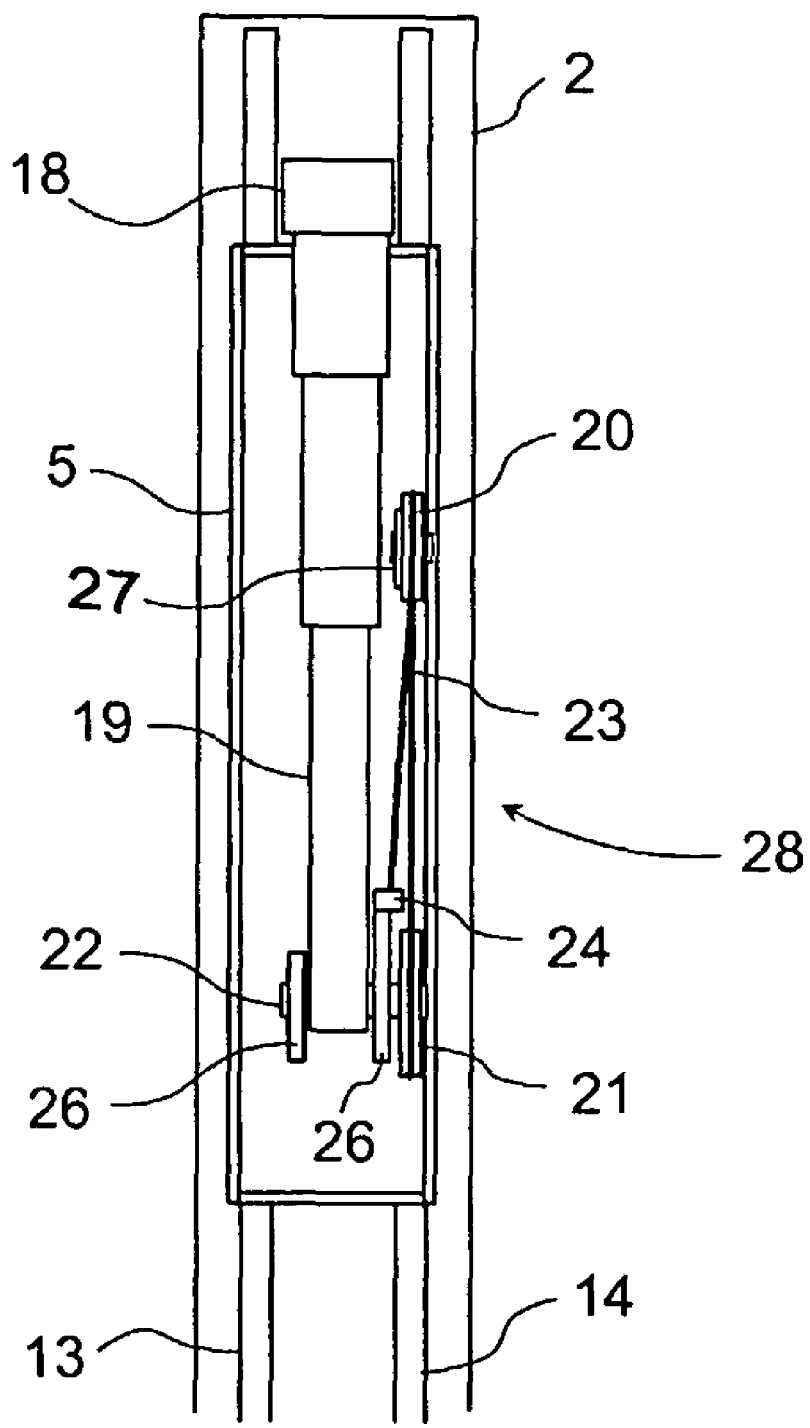

In the following, the invention will be described in more detail by referring to an example and the attached drawings, wherein FIG. 1 presents an oblique top view of a typical panoramic X-ray apparatus in which the solution of the invention can be applied, FIG. 2 presents a simplified front view of another panoramic X-ray apparatus in which the solution of the invention is applied, FIG. 3 presents a simplified and partially sectioned lateral view of the equipment solution of the invention, and FIG. 4 presents a simplified and partially sectioned front view of the equipment solution of the invention.

FIG. 1 represents one typical panoramic X-ray apparatus 1 in which the solution of the invention can be applied. The main parts of the apparatus are a support element 2 arranged to remain substantially immovably in place and a support structure 4 supporting an imaging station 4a and arranged to be vertically movable, the guidance, for its motion being obtained from the support element 2. In the solution according to FIG. 1, the support element 2 is a column-type support pillar mounted with a support device 3 on a floor. However, the support element 2 could as well be mounted e.g. on a wall.

The vertically moving support structure 4 comprises at least a frame part 5 fitted to rest on the support element 2 and to carry a patient support 9, and a cantilever element 6 arranged to support at least an imaging arm assembly, which comprises at least a so-called C-arm 7, a mechanism 8 for supporting and moving the C-arm, an X-radiation source 10 and an image information receiving means 11. In addition, the apparatus comprises a user interface 12, which is used to control the vertical motion of the support structure 4 and the movements of the imaging arm assembly.

FIG. 2 presents a simplified front view of a panoramic X-ray apparatus 1 in which the solution of the invention is applied. As to its main parts and their functions, the solution illustrated in FIG. 2 corresponds to the panoramic X-ray apparatus presented in FIG. 1. In FIG. 2, the actuator 15 according to the invention, which is mounted in the frame part 5 of the support structure 4 and which produces the linear vertical motion of the frame part 5 of the support structure 4 and at the same time the vertical motion of the imaging station 4a; is depicted with broken lines for the sake of clarity. The construction of the actuator 15 producing linear motion and the construction of the support element 2 will be described in greater detail in connection with FIGS. 3 and 4. Cut through the front wall of the support element 2 serving as a support pillar is a substantially vertical elongated first slot 13, through which the frame part 5 of the support structure 4 is slidably supported on an essentially vertical sliding guide rail provided inside the support element 2. Cut through the front wall of the support element 2 serving as a support pillar is additionally a substantially vertical elongated second slot 14, through which a lower pulley of the actuator 15 inside the frame part 5 of the support structure 4 is arranged to be disposed partially inside the support element 2. The height of the slots 13 and 14 is at least substantially equal to the length of the range of vertical motion of the frame part 5 of the support structure 4.

FIGS. 3 and 4 present partially sectioned and simplified lateral and front views of the upper part of an panoramic X-ray apparatus 1 of the invention in a situation where the frame part 5 of the support structure 4 supporting the imaging station 4a is nearly at its highest position. The frame part 5 of the support structure 4 is e.g. a mainly closed box structure having in one side-wall an openable door, which is not shown in the figures. In FIG. 3, that wall of the box structure and the support element 2 which faces towards the viewer, and in FIG. 4 that wall of the box structure which faces towards the viewer, are omitted for better visualization.

As stated above, the frame part 5 of the support structure 4 is slidably supported on a substantially vertical sliding guide rail 16 inside-the support element 2 by means of one or more sliding guides 17. Inside the box structure of the frame part 5, the aforesaid actuator 15 producing the linear motion is mounted in such manner that the actuator 15 is arranged to move vertically with the box structure of the frame part 5. The actuator 15 comprises at least a dynamic power unit 18, such as an electric motor or equivalent, and a moving element 19 moving linearly in a vertical direction relative to the power unit 18, the free lower end of said moving element 19 being arranged to move both in the direction away from the power unit 18 and in the direction towards the power unit 18, the moving element being driven by the power unit. The actuator 15 producing linear motion is preferably e.g. a spindle motor.

In addition, disposed mainly inside the box structure of the frame part 5 is a transmission mechanism 28, which comprises at least an upper first diverting pulley 20 attached to the box structure of the frame part 5, a lower second diverting pulley 21 attached to the lower end of the moving element 19 of the linear actuator 15, and a suspension cable fitted to run around the said diverting pulleys 20, 21 and functioning as a flexible suspension element 23, the first end of which is secured to a fastening point 24 on a fastening element 26 placed at the lower end of the moving element 19 of the linear actuator 15 so as to be movable with the moving element 19, and the second end of which suspension cable 23 is immovably secured to a fastening point 25 at the upper end of the support element 2. Arranged in this way, the diverting pulleys 20 and 21 and the suspension element 23 are fitted to form a tackle type structure, whose action is such that the speed of vertical motion of the box structure of the frame part 5 and at the same time its travel distance are substantially greater than the speed and travel distance of the lower end of the moving element 19 of the actuator 15 when the lower end is in vertical motion. From this it also follows that, during vertical motion of the imaging station 4a, the speed of vertical motion of the support structure 4 is substantially greater than the speed of the vertical motion imparted by the actuator to the transmission mechanism 28. Correspondingly, the travel distance of the support structure 4 during vertical motion is substantially greater than the travel distance through which the lower end of the moving element 19 moves at the same time.

The first diverting pulley 20, secured to the box structure of the frame part 5 by means of fastening elements 27, is mounted with bearings so as to be rotatable about its central axis, and similarly the second diverting pulley 21, secured with fastening elements 26 to the lower end of the moving element 19, is mounted with bearings so as to be rotatable about its central axis 22. The suspension element 23 is so arranged that it runs from the fastening point 24 of its first end upwards to the first diverting pulley 20, passes over and around the first diverting pulley 20 and then goes down to the second diverting pulley 21, passes under and around the second diverting pulley 21 and finally goes up to the fastening point 25 of its second end on the support element 2.

The distance between the first diverting pulley 20 and the second diverting pulley 21 is arranged to be variable by means of the actuator 15 during the vertical motion of the imaging station 4a in such manner that the second diverting pulley 21 attached to the lower end of the moving element 19 moves vertically together with the free lower end of the moving element 19. For the vertical movement of the second diverting pulley 21, the back wall of the box structure of the frame part 5, i.e. the wall facing towards the support element 2, is provided with a substantially vertical, elongated and slot-like aperture disposed essentially in the same vertical plane as slot 14 in the support element 2, the width of the aperture being suitably larger than the thickness of the second diverting pulley 21. For the sake of clarity, the aperture is not shown in the figures. The second diverting pulley 21 is so positioned and dimensioned that part of the diverting pulley 21 is inside the box structure of the frame part 5 while part of the diverting pulley 21 is inside the support element 2. The second diverting pulley 21 thus extends from inside the box structure of the frame part 5 into the support element 2 through the aforesaid back wall aperture and the slot 14.

With the above-described construction, the transmission ratio of velocity and travel distance is 1:3. Thus, for example, when the lower end of the moving element 19 moves vertically downwards through 10 cm, the frame part 5 of the support. structure 4 and at the same time the imaging station 4a together with all the associated devices and the patient support 9 arranged to move with the support structure 4 move vertically downwards through 30 cm. The above-mentioned travel distance of about one meter required for the imaging station 4a is here implemented according to the invention by using an arrangement where the vertically movable moving element 19 of the actuator 15 is arranged to produce, by its own vertical motion of about 25-35 cm, a vertical movement of about 75-105 cm for at least the imaging station 4a, and for the patient support 9 as well if the patient support is mounted to be movable with the support structure 4, i.e. a movement sufficient for patients of practically any size to be imaged. The transmission ratio can be easily changed by increasing the number of turns of the suspension cable around the diverting pulleys 20 and 21. For example, by making one additional turn, a transmission ratio of 1:5 is obtained, and so on.

It is obvious to a person skilled in the art that the invention is not limited to the exemplary embodiment described above but that it can be varied within the scope of the claims presented below. Thus, for example, the actuator producing the linear motion may be a different actuating device than a spindle motor. It may be e.g. a pneumatic or hydraulic actuator or e.g. some other mechanical or non-mechanical actuator suited to the purpose. The actuator is only required to produce a force adequate to enable vertical motion velocity and vertical travel distance of the imaging station sufficient for practical examining work, to be accomplished by using the transmission mechanism in conjunction with the actuator.

It is also obvious to a person skilled in the art that the construction and operation of the transmission mechanism may differ from the above description. Thus, instead of a tackle type structure, the transmission mechanism may be some other structure producing a transmission ratio.

It is additionally obvious to a person skilled in the art that, instead of a suspension cable as used in the tackle type structure, different kind of belts or chains can be used as a suspension and transmission element, in which case also the diverting pulleys are belt or chain pulleys corresponding to the suspension element instead of cable pulleys.

It is further obvious to a skilled person that regarding the transmission ratio of change of the velocity and the travel distance, it may be other than 1:3 or 1:5 as mentioned above. The transmission ratio may be any ratio within the range 1:n, where n is greater than one, suitably e.g. between 2-7 and preferably e.g. 3, in which case an optimal construction is achieved which provides a velocity/travel distance of vertical motion of the imaging station that is sufficient for patients of any size to be imaged and which enables a good performance to be achieved using an inexpensive actuator of reasonable power and size.

The invention claimed is:

1. A panoramic X-ray apparatus, comprising at least a support element, a patient support arranged to be movable in a vertical direction and an imaging station, which panoramic X-ray apparatus has a support structure arranged to support at least the imaging station, and which panoramic X-ray apparatus has an actuator producing a vertical linear motion for moving at least the imaging station to different height positions, characterized in that the panoramic X-ray apparatus comprises a transmission mechanism which affects the velocity/travel distance of the vertical movement of the imaging station and which is connected at least to the actuator and either to the aforesaid support structure or to the aforesaid support element in such manner that the velocity/travel distance of the vertical movement of the imaging station is substantially greater than the velocity/travel distance of the motion imparted by the actuator to the transmission mechanism, the transmission mechanism comprising at least a first diverting pulley and a second diverting pulley, wherein a distance between the first diverting pulley and the second diverting pulley is arranged to be variable by means of the actuator during vertical movement of the imaging station.

2. The panoramic X-ray apparatus according to claim 1, characterized in that the transmission mechanism is a tackle type structure comprising the at least the first diverting pulley and the second diverting pulley and a substantially flexible suspension element arranged to run around the diverting pulleys.

3. The panoramic X-ray apparatus according to claim 2, characterized in that a first end of the flexible suspension element is secured to a vertically movable moving element of the actuator by means of a fastening element, from which the suspension element is passed at least once over each diverting pulley, after which a second end of the suspension element is passed to its fastening point on the support element.

4. The panoramic X-ray apparatus according to claim 1, characterized in that the actuator is attached to the support structure so as to be movable with the support structure during vertical motion, and that the second diverting pulley of the transmission mechanism is attached to a vertically movable moving element of the actuator.

5. The panoramic X-ray apparatus according to claim 1, characterized in that the transmission mechanism has a transmission ratio of 1:n, where n is greater than one.

6. The panoramic X-ray apparatus according to claim 1, characterized in that a vertically movable moving element of the actuator is arranged to produce a vertical movement in a travel distance range of about 25-35 cm, said vertical movement being arranged to affect, via the transmission mechanism with a transmission ratio of 1:3, at least the vertical motion of the imaging station.

7. The panoramic X-ray apparatus according to claim 2, characterized in that the suspension element is a cable-like, belt-like or band-like structure and that the structure of the diverting pulleys is adapted to match the said suspension element structures.

8. The panoramic X-ray apparatus according to claim 1, characterized in that the actuator is a spindle motor, a pneumatic actuator, a hydraulic actuator or some other mechanical or non-mechanical actuator suited to the purpose, producing a substantially linear motion.

9. A panoramic X-ray apparatus, comprising at least a support element, a patient support arranged to be movable in a vertical direction and an imaging station, which panoramic X-ray apparatus has a support structure arranged to support at least the imaging station, and which panoramic X-ray apparatus has an actuator producing a vertical linear motion for moving at least the imaging station to different height positions, characterized in that the panoramic X-ray apparatus comprises a transmission mechanism which affects the velocity/travel distance of the vertical movement of the imaging station and which is connected at least to the actuator and either to the aforesaid support structure or to the aforesaid support element in such manner that the velocity/travel distance of the vertical movement of the imaging station is substantially greater than the velocity/travel distance of the motion imparted by the actuator to the transmission mechanism, wherein the actuator is attached to the support structure so as to be movable with the support structure during vertical movement and a second diverting pulley of the transmission mechanism is attached to a vertical movable moving element of the actuator.

10. The panoramic X-ray apparatus according to claim 9, characterized in that the transmission mechanism is a tackle type structure comprising the at least the first diverting pulley and the second diverting pulley and a substantially flexible suspension element arranged to run around the diverting pulleys.

11. The panoramic X-ray apparatus according to claim 10, characterized in that the first end of the flexible suspension element is secured to a vertically movable moving element of the actuator by means of a fastening element, from which the suspension element is passed at least once over each diverting pulley, after which the second end of the suspension element is passed to its fastening point on the support element.

12. The panoramic X-ray apparatus according to claim 9, characterized in that the transmission mechanism has a transmission ratio of 1:n, where n is greater than one.

13. The panoramic X-ray apparatus according to claim 9, characterized in that the vertically movable moving element of the actuator is arranged to produce a vertical movement in a travel distance range of about 25-35 cm, said vertical movement being arranged to affect, via the transmission mechanism with a transmission ratio of 1:3, at least the vertical motion of the imaging station.

14. The panoramic X-ray apparatus according to claim 10 characterized in that the suspension element is a cable-like, belt-like or band-like structure and that the structure of the diverting pulleys is adapted to match the said suspension element structures.

15. The panoramic X-ray apparatus according to claim 9 characterized in that the actuator is a spindle motor, a pneumatic actuator, a hydraulic actuator or some other mechanical or non-mechanical actuator suited to the purpose, producing a substantially linear motion.

* * * * *